United States Patent [19]

Toth et al.

[11] Patent Number: 5,450,462
[45] Date of Patent: Sep. 12, 1995

[54] MODULATION OF X-RAY TUBE CURRENT DURING CT SCANNING WITH MODULATION LIMIT

[75] Inventors: Thomas L. Toth, Brookfield; Jonathan R. Schmidt, Wales, both of Wis.

[73] Assignee: General Electric Company, Milwaukee, Wis.

[21] Appl. No.: 301,103

[22] Filed: Sep. 6, 1994

Related U.S. Application Data

[63] Continuation-in-part of Ser. No. 155,037, Nov. 19, 1993, Pat. No. 5,379,333.

[51] Int. Cl.$^6$ .............................................. A61B 6/00
[52] U.S. Cl. ..................................... 378/16; 378/8; 378/108
[58] Field of Search ............... 378/4, 8, 16, 20, 108, 378/109, 110, 111, 112, 145–147, 150–151

[56] References Cited

U.S. PATENT DOCUMENTS

| | | | |
|---|---|---|---|
| 4,624,007 | 11/1986 | Muranushi | 378/20 X |
| 5,103,469 | 4/1992 | Tanaka | 378/16 |
| 5,379,333 | 1/1995 | Toth | 378/16 |

OTHER PUBLICATIONS

U.S. patent application Ser. No. 854,227, filed May 19, 1986 and entitled "Dynamic Flux Intensity Control in Computer Tomography Systems".

*Primary Examiner*—David P. Porta
*Attorney, Agent, or Firm*—Quarles & Brady

[57] ABSTRACT

An x-ray CT system modulates x-ray tube current as a function of gantry angle to reduce the total patient dose without significantly increasing image noise. A scout scan is performed to acquire attenuation data which enables an optimal current modulation profile to be calculated for each slice in the scan. The modulation profile is clipped when the modulation limit of the x-ray generator is reached.

6 Claims, 3 Drawing Sheets

MODULATION OF X-RAY TUBE CURRENT DURING CT SCANNING WITH MODULATION LIMIT

RELATED APPLICATION

This application is a continuation-in-part of U.S. patent application Ser. No. 155,037, filed on Nov. 19, 1993, and entitled "*Variable Dose Application By Modulation Of X-Ray Tube Current During CT Scanning*" now U.S. Pat. No. 5,379,333.

BACKGROUND OF THE INVENTION

The present invention relates to computed tomography (CT) imaging apparatus; and more particularly, to reducing the x-ray dose applied to a patient without significantly increasing noise artifacts in the image.

In a computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one or more revolutions of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a cathode ray tube display.

Quantum noise degrades the diagnostic quality of a CT image and this noise is related to the amount of x-rays, or "dose", employed to acquire the attenuation measurements, and to the attenuation characteristics of the patient. Image artifacts due to noise will increase if the x-rays measured at the detector drop to low levels either because the prescribed x-ray dose is too low or the beam is highly attenuated by patient anatomy. The x-ray dose is controlled by the current ("mA") applied to the x-ray tube, and the practice is to fix this current at a level which provides a constant dose during the entire scan. If the operator prescribes a high dose, image quality is superb throughout, but excessive x-ray flux is produced during portions of the scan when patient attenuation is low. The patient is thus exposed to an excessive dose and the x-ray tube is unnecessarily heated. On the other hand, if the dose is reduced (to prevent tube overheating during the prescribed scan), noise artifacts will appear in the image oriented at locations where the beam is highly attenuated. For example, horizontal streaks may appear in slices through a patient's shoulders and hips.

In the above-cited co-pending application, a modulation profile for use in scanning a patient with minimal dose and a clinically insignificant noise increase is calculated. A transverse slice through a patient may be viewed radiologically as an oval shape having major and minor axes which change along the length of the patient. For example, at the hips the major axis is horizontal and much longer than the vertical minor axis, whereas at the neck, the major axis is vertical and only a little longer than the minor axis. At other locations the radiological profile may be nearly circular. A general purpose modulation template having a substantially sinusoidal shape at twice the frequency of the gantry rotation may be automatically tailored to such radiological profiles by acquiring during a "scout" scan two orthogonal views through the transverse slice prior to the scan. This information is employed to produce a modulation profile from the sinusoidal template.

Unfortunately, it is not possible for the x-ray tube and generator to modulate the x-ray dose below a certain level during a scan. Cycling the tube current over a large current range can lead to thermal fatigue of the x-ray tube filament and increasing the response time of the closed current control loop in the generator in order to achieve deeper modulation increases the instability of the closed tube voltage control loop. In addition, the shape of the modulation waveform actually produced at higher modulation levels is not consistent between tube/generator combinations. As a result, potential dose reduction is not fully realized in situations that allow modulation of the dose below this practical limit.

SUMMARY OF THE INVENTION

The present invention relates to a CT imaging system in which the x-ray dose is modulated as the gantry is rotated during a scan such that a prescribed noise level is better maintained in all of the acquired attenuation measurements. More specifically, a modulation profile which is indicative of the variations in patient attenuation during a revolution of the gantry is employed during the scan to modulate x-ray tube current as a function of gantry rotation to dynamically modulate the dose as required by the patient's anatomy. When the modulation profile requires dose modulation below a preset limit at certain gantry angles, the modulation profile is altered to increase dose modulation at other gantry angles. This altered modulation profile is employed to calculate the optimal tube current at a series of gantry angles and each calculated tube current that exceeds the modulation limit of the x-ray source is limited to a minimum level which the x-ray source can produce.

A general object of the present invention is to clip the modulation profile when the x-ray source cannot be modulated enough to reduce the dose to the level indicated. The ability of the x-ray tube and its current supply to respond to the modulation profile may be limited. For example, a 50% modulation may be the limit. It is a teaching of the present invention that the modulation profile is followed to calculate the x-ray tube current commands, but the current commands are limited to a minimum level set by a modulation limit.

It is another object of the present invention to recapture some of the dose reduction that is lost due to the clipping of the modulation profile at the modulation limit. This is achieved by altering the modulation profile to increase-dose reduction at gantry angles that do not require clipping of the modulation profile.

DESCRIPTION OF THE PREFERRED EMBODIMENT

Figure 1:
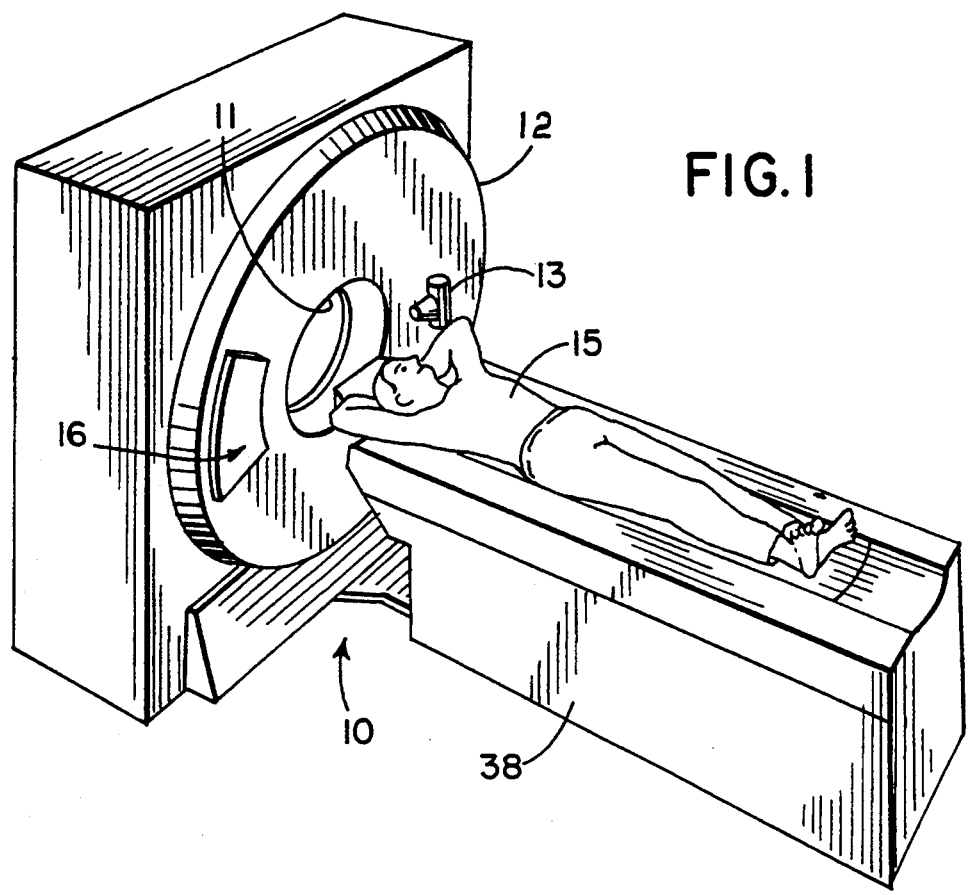
FIG. 1 is a pictorial view of a CT imaging system in which the present invention may be employed.
Figure 2:
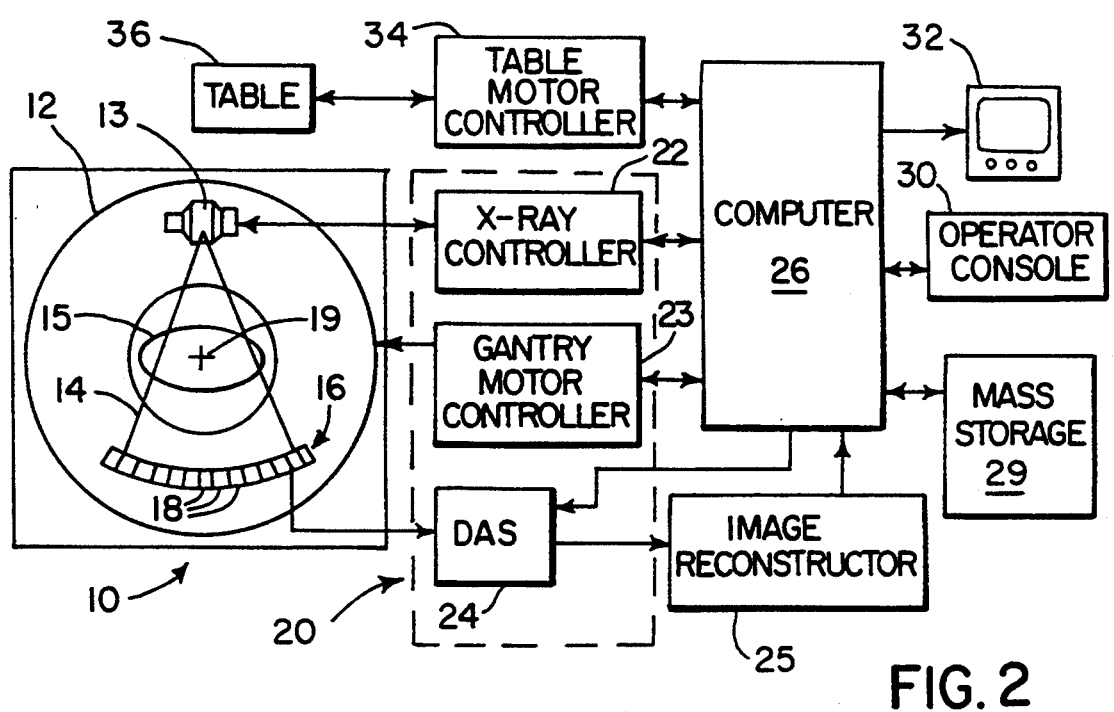
FIG. 2 is a block schematic diagram of the CT imaging system.

With initial reference to FIGS. 1 and 2, a computed tomography (CT) imaging system 10 includes a gantry 12 representative of a "third generation" CT scanner. Gantry 12 has an x-ray source 13 that projects a beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15. A reference detector at one end of the array 16 measures the unattenuated beam intensity during the scan to detect variations in the applied x-ray dose. This reference data is used in subsequent processing of the x-ray projection data to normalize it to a common reference dose.

The rotation of the gantry and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction. The reconstructed image is applied as an input to a computer 26 which stores the image in a mass storage device 29.

The computer 26 also receives commands and scanning parameters from an operator via console 30 that has a keyboard. An associated cathode ray tube display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12.

Figure 4:
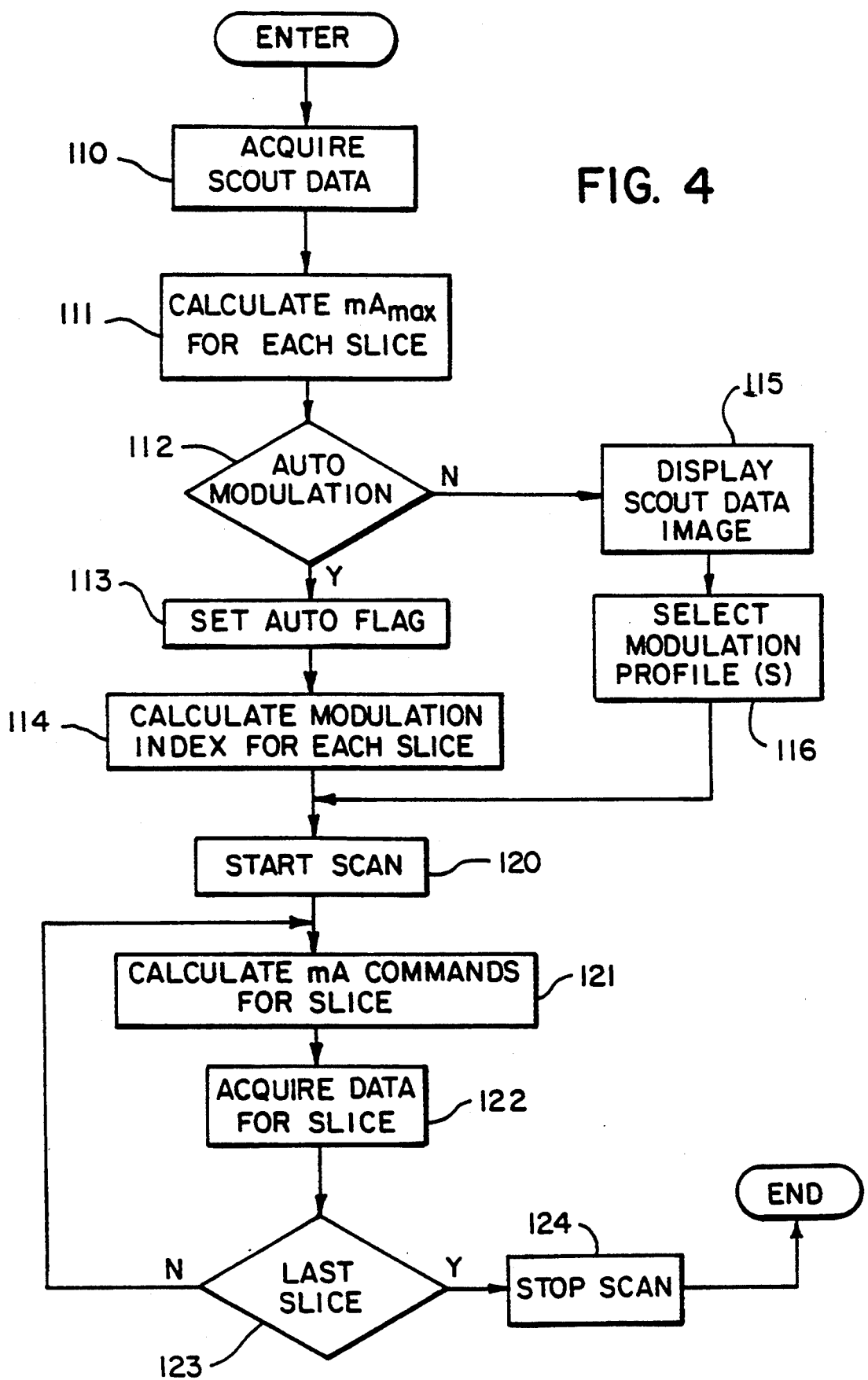
FIG. 4 is a flow chart of a program executed by the CT imaging system of FIG. 2 to carry out the preferred embodiment of the invention.

Referring particularly to FIG. 2, the computer 26 directs the system components to carry out the prescribed scan in accordance with stored programs. If an mA modulation strategy is selected by the operator, the program illustrated by the flow chart in FIG. 4 is executed by computer 26 to implement the preferred embodiment of the present invention. The first step is to acquire scout data, as indicated at process block 110. This scout data is comprised of two orthogonal views from each slice in the prescribed scan, one at a gantry angle of 0° and the other at an angle of 90°. The next step, as indicated at process block 111, is to calculate the maximum x-ray tube current ($mA_{max}$) for each slice using the scout data as described in copending U.S. patent application Ser. No. 08/155,045 filed on Nov. 19, 1993 and entitled "*Dynamic Dose Control In Multi-Slice CT Scan.*" This enables the x-ray dose to be reduced for slices with reduced attenuation of the x-ray beam without exceeding the prescribed image noise. It results in an array of stored values ($mA_{max}$), one for each of the respective slices in the scan.

As indicated at decision block 112, the operator is then signalled to indicate if automatic modulation is to be applied during the scan, and if so, a flag is set at process block 113 and a modulation index ($\alpha$) is calculated for each slice as indicated at process block 114. The modulation index ($\alpha$) is calculated from the scout data and it indicates the degree to which x-ray tube current can be modulated without significantly increasing noise artifacts in the reconstructed image. As described in the above-cited parent application, the attenuation ratio is calculated from the acquired scout data and this ratio is used as an index into a stored table of modulation indices ($\alpha$). This table of modulation indices vs attenuation ratio is generated empirically to produce a small amount of noise increase in the image (i.e. 5%). This table is computed once and is provided as part of the system software.

Figure 3:
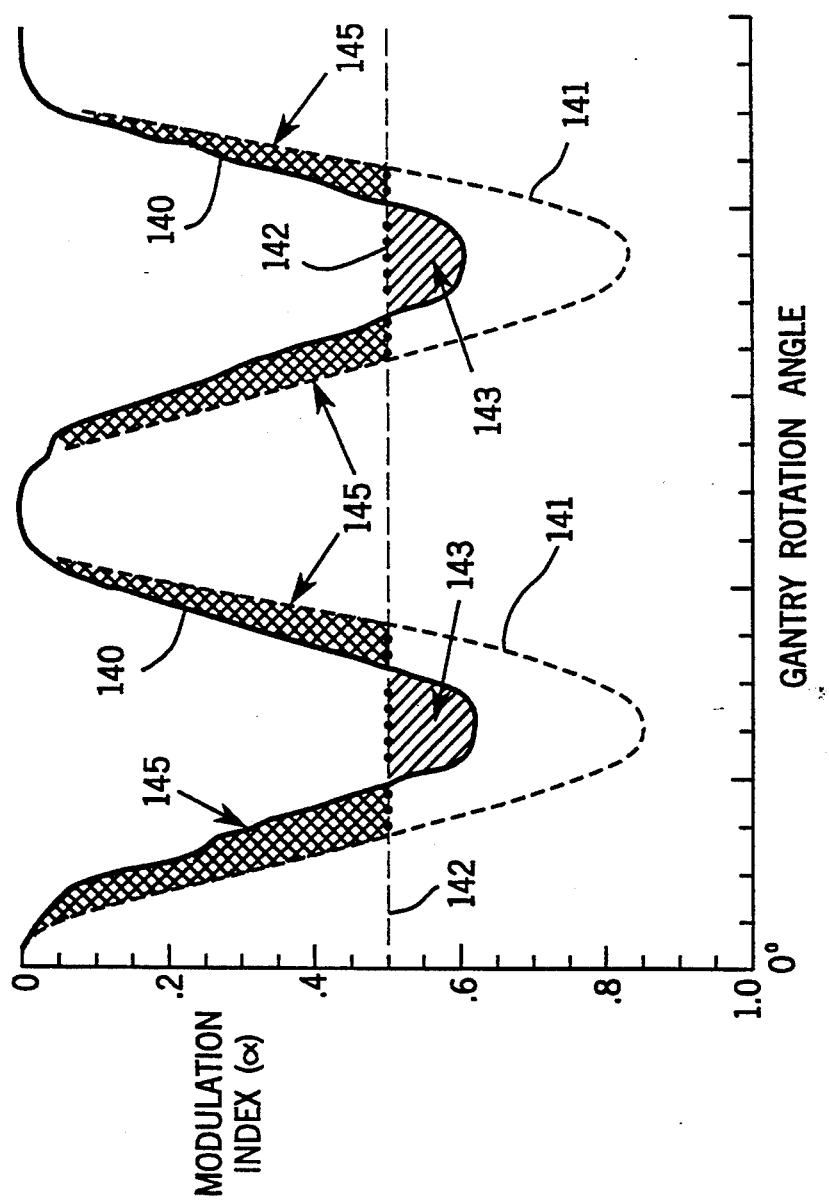
FIG. 3 is a graphic representation of a sinusoidal modulation profile employed in the preferred embodiment of the invention.

It is a teaching of the present invention that the modulation index ($\alpha$) should be increased when the modulation limit of the system will be exceeded. Referring to FIG. 3, for example, if the calculated attenuation ratio is 60, a modulation index of 0.60 is read from the stored table and will produce the modulation profile indicated by solid line 140. However, because the dose cannot be modulated below a certain limit (in the preferred embodiment 0.5) indicated by dashed line 142, a dose reduction indicated by section lines 143 is not realized. According to the present invention this lost dose reduction is offset by increasing the x-ray index $\alpha$ to 0.85 as indicated by dashed line 141. This modulation index is chosen because the dose reduction indicated by cross hatched areas 145 is substantially the same as the areas 143.

This alteration of the modulation index ($\alpha$) is achieved by modifying the stored table.

| Attenuation Ratio | Optimal $\alpha$ | Altered $\alpha$ |
| --- | --- | --- |
| 1.0 | 0.0 | 0.0 |
| 1.5 | .10 | .1 |
| 2.9 | .2 | .2 |
| 6.3 | .25 | .26 |
| 14.9 | .33 | .358 |
| 28.7 | .44 | .475 |
| 60 | .60 | .85 |
| 70 | .638 | 100 |

During patient scanning, the attenuation ratio determines the index into this table (which is linearly interpolated between entries) to produce the altered modulation index ($\alpha$). This altered modulation index ($\alpha$) is used to produce a clipped modulation profile as will be described below.

If the automatic mode is not selected, the system branches at decision block 112 and the scout data is employed to produce an image for the operator at process block 115. This image enables the operator to locate the prescribed slices with respect to the patient's anatomy and to manually select appropriate x-ray tube current modulation profiles at process block 116. In the preferred embodiment, the modulation profiles are stored as forty values which, when multiplied by the maximum tube current ($mA_{max}$) calculated above, provide forty current commands for the x-ray controller 22 that determine x-ray tube current at forty successive 9° segments of gantry revolution.

Referring still to FIGS. 2 and 4, regardless of the modulation profile selected, the computer 26 starts the scan at process block 120, by signaling the gantry motor controller 23. It then enters a loop in which the forty mA commands are calculated at process block 121 and downloaded to the x-ray controller 22. When the auto mode has been selected, this step involves the application of the modulation index ($\alpha$) calculated above and the maximum current ($mA_{max}$) also calculated above to a general purpose sinusoidal template expressed as follows:

$$mA = mA_{max}[(1-\alpha) + \alpha\cos(2\ wt + \phi)] \quad (1)$$

where:

$mA_{max}$ = the tube current without modulation,
$\alpha$ = modulation index calculated from the scout data;
$wt$ = gantry angle ($\theta$) at time t, and
$\phi$ = starting phase in the sinusoidal template determined from the scout data.

The forty mA commands calculated according to Eq. (1) will produce a substantially sinusoidal variation in x-ray tube current as shown by the curve 140 in FIG. 3. However, it may not be possible to modulate x-ray tube current below a certain level because of limitations inherent in the x-ray tube 13 and the x-ray controller 22. For example, in the preferred embodiment a modulation of 50% of $mA_{max}$ is the limit, and the modulation waveform is clipped at this level.

The clipping of the modulation waveform according to the present invention is accomplished by calculating the forty mA commands according to Eq. (1) using the altered modulation index ($\alpha$) read from the stored table as described above. A minimum mA command ($mA_{min}$) is then calculated according to the following expression based on the known generator modulation limit ($\alpha_{lim}$):

$$mA_{min} = mA_{max}(1 - \alpha_{lim}) \quad (2)$$

The calculated mA command is then compared with this minimum mA command, and if it is less than $mA_{min}$, it is replaced by the minimum current command $mA_{min}$:

$$mA = mA_{min}. \quad (3)$$

The modulation waveform indicated by the modulation index ($\alpha$) is thus faithfully followed until the generator limits are reached. At this point the waveform is clipped at $mA_{min}$.

As shown in FIG. 4 at process block 122, the resulting forty mA values are downloaded to the x-ray controller 22 and a timing signal is sent to coordinate the start of the dose with gantry orientation and table position.

As each slice is acquired the gantry 12 is rotated at a constant angular rate by the gantry motor controller 23. At the completion of each 9° increment of gantry rotation the next mA current command downloaded to the x-ray controller 22 is read out and used to control x-ray tube current during the next 9° increment of rotation. This cycle continues until all forty mA current commands have been applied in succession as the gantry completes a 360° rotation.

The cycle of calculating mA current commands and downloading them to the x-ray controller 22 continues until the last slice in the prescribed scan is acquired as detected at decision block 123. The gantry is then stopped at process block 124 and the operator is signaled that the scan is finished.

The acquired x-ray profile data is processed in the usual fashion to reconstruct a slice image. Even though the views are acquired with varying x-ray beam intensity, the data is normalized with the reference detector signal as mentioned above so that the reconstruction of the image is performed with x-ray profile data that is effectively acquired with a constant x-ray beam intensity during the entire gantry revolution.

It should be apparent to those skilled in the art that many modifications can be made to the preferred embodiment described herein without departing from the spirit of the invention. For example, other preset modulation profiles and sampling resolutions may be stored and presented to the operator for use during the scan. Also, while the sinusoidal shape at twice the gantry frequency is preferred as the general purpose template, other shapes are possible. Also, the patient projection data may be acquired in a helical survey scan or from an adjacent slice which has already been acquired. It should also be apparent that the present invention is applicable to a CT system which acquires each slice either while the patient table is stationary or in a spiral scan in which the table is moved continuously throughout the data acquisition.

We claim:

1. A method for reducing the dose of an x-ray beam applied to a patient by an x-ray CT system during the acquisition of attenuation data from a slice, the steps comprising:
   a) acquiring patient attenuation data from the slice which indicates patient attenuation of the x-ray beam at two substantially orthogonal gantry angles;
   b) calculating a modulation index ($\alpha$) using information derived from the acquired patient attenuation data which indicates the reduction in x-ray dose applicable to the patient;
   c) calculating a modulation profile using the modulation index ($\alpha$), the modulation profile including a set of values which indicate the x-ray dose applied to the patient at successive gantry angles during the acquisition of attenuation data from the single slice;
   d) comparing each value in the modulation profile with a value indicative of minimum x-ray dose, and when the modulation profile value is less, replacing said modulation profile value with the value indicative of the minimum x-ray dose; and
   acquiring the attenuation data for the slice by rotating the gantry and modulating the applied x-ray dose as indicated by the modulation profile.

2. The method as recited in claim 1 in which the x-ray dose is modulated by changing the current supplied to an x-ray tube.

3. The method as recited in claim 1 in which the modulation profile varies the x-ray dose substantially sinusoidally as a function of gantry angle.

4. The method as recited in claim 1 in which the set of values in the modulation profile indicate current applied to an x-ray tube at successive gantry angles, and the value indicative of a minimum x-ray dose is indicative of the lowest current which can be applied to the x-ray tube without departing from the current values indicated by the modulation profile.

5. The method as recited in claim 1 in which step b) is performed by
   i) calculating an attenuation ratio from the acquired patient attenuation data; and
   ii) selecting the modulation index ($\alpha$) from a stored table of values using the calculated attenuation ratio.

6. The method as recited in claim 5 in which the modulation index values stored in said table increases as a function of increasing attenuation ratio.

* * * * *